United States Patent
Kelley et al.

(10) Patent No.: US 7,887,557 B2
(45) Date of Patent: Feb. 15, 2011

(54) CATHETER HAVING A CUTTING BALLOON INCLUDING MULTIPLE CAVITIES OR MULTIPLE CHANNELS

(75) Inventors: Gregory S. Kelley, San Diego, CA (US); Show-Mean Wu, San Diego, CA (US); Ricardo David Roman, San Diego, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2003 days.

(21) Appl. No.: 10/641,955

(22) Filed: Aug. 14, 2003

(65) Prior Publication Data

US 2005/0038383 A1 Feb. 17, 2005

(51) Int. Cl.
*A61B 17/22* (2006.01)
(52) U.S. Cl. ............................ 606/159; 604/96.01
(58) Field of Classification Search ............ 606/159, 606/192, 194; 604/96.01, 103, 103.06, 103.08, 604/915, 96, 103.01, 508, 533
See application file for complete search history.

(56) References Cited

U.S. PATENT DOCUMENTS

| | | | |
|---|---|---|---|
| 2,816,552 A | 12/1957 | Hoffman | |
| 3,174,851 A | 3/1965 | Buehler et al. | |
| 3,351,463 A | 11/1967 | Rozner et al. | |
| 3,635,223 A | 1/1972 | Klieman | |
| 3,749,085 A | 7/1973 | Willson et al. | |
| 3,753,700 A | 8/1973 | Harrison et al. | |
| 3,990,453 A | 11/1976 | Douvas et al. | |
| 4,140,126 A | 2/1979 | Choudhury | |
| 4,141,364 A | 2/1979 | Schultze | |
| 4,263,236 A | 4/1981 | Briggs et al. | |
| 4,273,128 A | 6/1981 | Lary | |
| 4,292,974 A | 10/1981 | Fogarty et al. | |
| 4,406,656 A | 9/1983 | Hattler et al. | |
| 4,465,072 A | 8/1984 | Taheri | |
| 4,490,421 A | 12/1984 | Levy | |
| 4,572,186 A | 2/1986 | Gould et al. | |
| 4,574,781 A | 3/1986 | Chin | |
| 4,608,984 A | 9/1986 | Fogarty | |
| 4,627,436 A | 12/1986 | Leckrone | |
| 4,685,458 A | 8/1987 | Leckrone | |

(Continued)

FOREIGN PATENT DOCUMENTS

DE        34 00 416 A1        7/1985

(Continued)

OTHER PUBLICATIONS

Lary, Banning G., et al., "A Method for Creating a Coronary-Myocardial Artery," *Surgery*, Jun. 1966, vol. 59, No. 6, pp. 1061-1064.

(Continued)

*Primary Examiner*—Michael J Milano
*Assistant Examiner*—Victor X Nguyen
(74) *Attorney, Agent, or Firm*—Seager, Tufte & Wickhem, LLC

(57) ABSTRACT

An angioplasty balloon catheter and method of making and using the same. The balloon catheter may include a catheter shaft and a balloon coupled to the shaft. The balloon may include one or more cutting edges or member and may include a plurality of chambers defined therein.

10 Claims, 7 Drawing Sheets

U.S. PATENT DOCUMENTS

| | | |
|---|---|---|
| 4,686,982 A | 8/1987 | Nash |
| 4,696,667 A | 9/1987 | Masch |
| 4,705,517 A | 11/1987 | DiPisa, Jr. |
| 4,723,549 A | 2/1988 | Wholey et al. |
| 4,728,319 A | 3/1988 | Masch |
| 4,747,405 A | 5/1988 | Leckrone |
| 4,748,982 A | 6/1988 | Horzewski et al. |
| 4,784,636 A | 11/1988 | Rydell |
| 4,787,388 A | 11/1988 | Hofmann |
| 4,790,813 A | 12/1988 | Kensey |
| 4,793,348 A | 12/1988 | Palmaz |
| 4,796,629 A | 1/1989 | Grayzel |
| 4,799,479 A | 1/1989 | Spears |
| RE32,983 E | 7/1989 | Levy |
| 4,886,061 A | 12/1989 | Fischell et al. |
| 4,921,483 A | 5/1990 | Wijay et al. |
| 4,921,484 A | 5/1990 | Hillstead |
| 4,936,845 A | 6/1990 | Stevens |
| 4,966,604 A | 10/1990 | Reiss |
| RE33,561 E | 3/1991 | Levy |
| 5,009,659 A | 4/1991 | Hamlin et al. |
| 5,030,201 A | 7/1991 | Palestrant |
| 5,042,985 A | 8/1991 | Elliott et al. |
| 5,047,040 A | 9/1991 | Simpson et al. |
| 5,049,132 A | 9/1991 | Shaffer et al. |
| 5,078,722 A | 1/1992 | Stevens |
| 5,078,725 A | 1/1992 | Enderle et al. |
| 5,085,662 A | 2/1992 | Willard |
| 5,087,265 A | 2/1992 | Summers |
| 5,100,424 A | 3/1992 | Jang et al. |
| 5,100,425 A | 3/1992 | Fischell et al. |
| 5,102,390 A | 4/1992 | Crittenden et al. |
| 5,116,318 A | 5/1992 | Hillstead |
| 5,135,482 A | 8/1992 | Neracher |
| 5,152,773 A | 10/1992 | Redha |
| 5,156,594 A | 10/1992 | Keith |
| 5,156,610 A | 10/1992 | Reger |
| 5,158,564 A | 10/1992 | Schnepp-Pesch et al. |
| 5,176,693 A | 1/1993 | Pannek, Jr. |
| 5,180,368 A | 1/1993 | Garrison |
| 5,196,024 A * | 3/1993 | Barath ............... 606/159 |
| 5,197,965 A * | 3/1993 | Cherry et al. ............. 606/54 |
| 5,209,749 A | 5/1993 | Buelna |
| 5,209,799 A | 5/1993 | Vigil |
| 5,226,430 A | 7/1993 | Spears et al. |
| 5,226,887 A | 7/1993 | Farr et al. |
| 5,248,311 A | 9/1993 | Black et al. |
| 5,250,059 A | 10/1993 | Andreas et al. |
| 5,254,089 A | 10/1993 | Wang |
| 5,300,025 A | 4/1994 | Wantink |
| 5,308,323 A * | 5/1994 | Sogawa et al. ........ 604/95.03 |
| 5,318,576 A | 6/1994 | Plassche, Jr. et al. |
| 5,320,634 A | 6/1994 | Vigil et al. |
| 5,328,472 A | 7/1994 | Steinke et al. |
| 5,336,234 A | 8/1994 | Vigil et al. |
| 5,372,601 A | 12/1994 | Lary |
| 5,395,361 A | 3/1995 | Fox et al. |
| 5,411,466 A | 5/1995 | Hess |
| 5,415,654 A | 5/1995 | Daikuzono |
| 5,417,653 A | 5/1995 | Sahota et al. |
| 5,417,703 A | 5/1995 | Brown et al. |
| 5,425,711 A | 6/1995 | Ressemann et al. |
| 5,437,659 A | 8/1995 | Leckrone |
| 5,441,510 A | 8/1995 | Simpson et al. |
| 5,456,681 A | 10/1995 | Hajjar |
| 5,470,415 A * | 11/1995 | Perkins et al. .............. 156/196 |
| 5,496,308 A | 3/1996 | Brown et al. |
| 5,507,760 A | 4/1996 | Wynne et al. |
| 5,507,761 A | 4/1996 | Duer |
| 5,522,818 A | 6/1996 | Keith et al. |
| 5,522,825 A | 6/1996 | Kropf et al. |
| 5,549,556 A | 8/1996 | Ndondo-Lay et al. |
| 5,569,195 A | 10/1996 | Saab |
| 5,569,277 A | 10/1996 | Evans et al. |
| 5,571,087 A | 11/1996 | Ressemann et al. |
| 5,616,149 A | 4/1997 | Barath |
| 5,628,761 A | 5/1997 | Rizik |
| 5,643,296 A | 7/1997 | Hundertmark et al. |
| 5,645,529 A | 7/1997 | Fagan et al. |
| 5,681,336 A | 10/1997 | Clement et al. |
| 5,713,913 A | 2/1998 | Lary et al. |
| 5,718,684 A | 2/1998 | Gupta |
| 5,720,724 A | 2/1998 | Ressemann et al. |
| 5,792,105 A | 8/1998 | Lin et al. |
| 5,797,935 A * | 8/1998 | Barath ............... 606/159 |
| 5,814,016 A * | 9/1998 | Valley et al. ............. 604/96.01 |
| 5,827,201 A | 10/1998 | Samson et al. |
| 5,860,954 A | 1/1999 | Ropiak |
| 5,895,402 A | 4/1999 | Hundertmark et al. |
| 5,931,819 A | 8/1999 | Fariabi |
| 6,024,722 A | 2/2000 | Rau et al. |
| 6,039,699 A | 3/2000 | Viera |
| 6,066,149 A | 5/2000 | Samson et al. |
| 6,068,623 A | 5/2000 | Zadno-Azizi et al. |
| 6,139,510 A | 10/2000 | Palermo |
| 6,142,975 A | 11/2000 | Jalisi et al. |
| 6,165,140 A | 12/2000 | Ferrera |
| 6,165,167 A | 12/2000 | Delaloye |
| 6,165,292 A | 12/2000 | Abrams et al. |
| 6,168,571 B1 | 1/2001 | Solar et al. |
| 6,190,332 B1 | 2/2001 | Muni et al. |
| 6,193,686 B1 | 2/2001 | Estrada et al. |
| 6,217,549 B1 | 4/2001 | Selmon et al. |
| 6,217,567 B1 | 4/2001 | Zadno-Azizi et al. |
| 6,241,690 B1 | 6/2001 | Burkett et al. |
| 6,254,550 B1 | 7/2001 | McNamara et al. |
| 6,306,105 B1 | 10/2001 | Rooney et al. |
| 6,344,029 B1 | 2/2002 | Estrada et al. |
| 6,355,016 B1 | 3/2002 | Bagaoisan et al. |
| 6,379,362 B1 * | 4/2002 | Birk et al. .................... 606/73 |
| 6,383,146 B1 | 5/2002 | Klint |
| 6,387,075 B1 | 5/2002 | Stivland et al. |
| 6,398,798 B2 | 6/2002 | Selmon et al. |
| 6,409,863 B1 | 6/2002 | Williams et al. |
| 6,425,882 B1 | 7/2002 | Vigil |
| 6,458,076 B1 | 10/2002 | Pruitt |
| 6,471,673 B1 | 10/2002 | Kasterhofer |
| 6,533,754 B1 | 3/2003 | Hisamatsu et al. |
| 6,544,276 B1 | 4/2003 | Azizi |
| 7,008,438 B2 * | 3/2006 | O'Brien ............... 606/159 |

FOREIGN PATENT DOCUMENTS

| | | |
|---|---|---|
| DE | 3402573 | 8/1985 |
| DE | 35 19 626 A1 | 12/1986 |
| EP | 0 291 170 A1 | 11/1988 |
| EP | 0 414 350 A1 | 2/1991 |
| GB | 1 547 328 | 6/1979 |
| WO | WO 90/07909 A1 | 7/1990 |
| WO | WO 91/17714 A1 | 11/1991 |

OTHER PUBLICATIONS

Lary, Banning G., "A Method to Create and Correct Stenosis of a Coronary Artery," *Archives of Surgery*, Nov. 1966, vol. 93, pp. 828-830.

Lary, Banning G., "An Epicaridal Purse String Suture for Closing Coronary Arteriotomy," *The American Surgeon*, Mar. 1967, vol. 33, No. 3, pp. 213-214.

Lary, Banning G., "Coronary Artery Incision and Dilation," *Archives of Surgery*, Dec. 1980, vol. 115, pp. 1478-1480.

Lary, Banning G., "Coronary Artery Resection and Replacement by a Blood Conduit," *Surgery*, Apr. 1969, vol. 65, No. 4, pp. 584-589.

Lary, Banning G., "Effect of Endocardial Incisions on Myocardial Blood Flow," *Archives of Surgery*, Sep. 1963, vol. 87, pp. 424-427.

Lary, B.G., "Experimental Maintenance of Life by Intravenous Oxygen, Preliminary Report," *Clinical Congress of the American College of Surgeons*, San Francisco, Nov. 5-9, 1951, pp. 30-35.

Lary, Banning G., et al., "Experimental Vein Angioplasty of the Circumflex Coronary Artery," *Journal of Surgical Research*, Sep. 1974, vol. 17, No. 3, pp. 210-214.

Lary, Banning G., "Method for Increasing the Diameter of Long Segments of the Coronary Artery," *The American Surgeon*, Jan. 1966, vol. 32, No. 1, pp. 33-35.

Lary, Banning G., et al., "Myocardial Revascularization Experiments Using the Epicardium," *Archives of Surgery*, Jan. 1969, vol. 98, pp. 69-72.

Lary, Banning G., "Onlay Vein Graft for the Correction of Coronary Artery Obstruction," *Surgery*, Apr. 1966, vol. 59, No. 4, pp. 547-551.

Lary, Banning G., "Surgery for Coronary Artery Disease," *Nursing Clinics of North America*, Sep. 1967, vol. 2, No. 3, pp. 537-542.

Lary, Banning G., et al., "The 'Coronary Myocardial Artery' for Coronary Artery Disease," *Diseases of the Chest*, Apr. 1996, vol. 49, No. 4, pp. 412-419.

\* cited by examiner

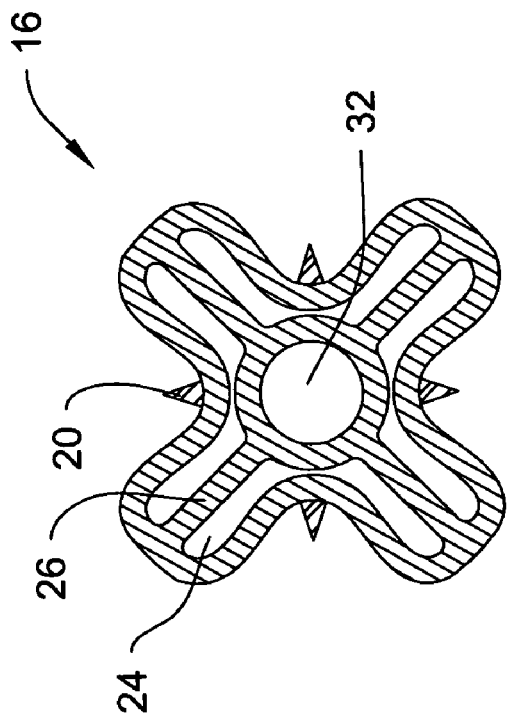
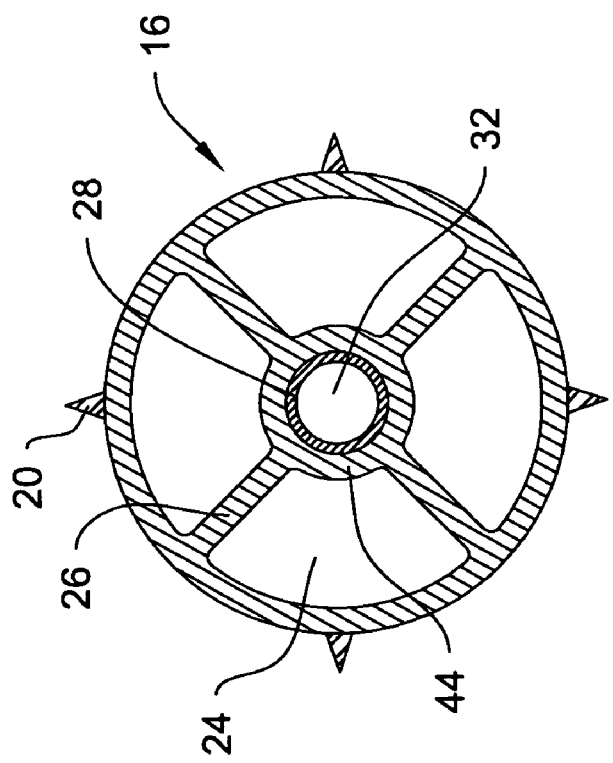

CATHETER HAVING A CUTTING BALLOON INCLUDING MULTIPLE CAVITIES OR MULTIPLE CHANNELS

FIELD OF THE INVENTION

The present invention pertains to angioplasty and angioplasty balloon catheters. More particularly, the present invention pertains to angioplasty balloon catheters that include one or more cutting edges coupled to the angioplasty balloon.

BACKGROUND OF THE INVENTION

Heart and vascular disease are major problems in the United States and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire so that the balloon is positioned adjacent a stenotic lesion. The balloon is then inflated and the restriction of the vessel is opened.

One of the major obstacles in treating coronary artery disease and/or treating blocked blood vessels is re-stenosis. Evidence has shown that cutting the stenosis, for example, with an angioplasty balloon equipped with a cutting blade, during treatment can reduce incidence of re-stenosis. Additionally, cutting the stenosis may reduce trauma at the treatment site and/or may reduce the trauma to adjacent healthy tissue. Cutting blades may also be beneficial additions to angioplasty procedures when the targeted occlusion is hardened or calcified. It is believed typical angioplasty balloons, alone, may not be able to expand certain of these hardened lesions. Thus, angioplasty balloons equipped with cutting edges have been developed to attempt to enhance angioplasty treatments. There is an ongoing need for improved angioplasty devices, including cutting angioplasty balloons, and improved methods of treating intravascular stenoses and occlusions.

Another potential obstacle that may accompany treatments that include expansion of a stenosis with an angioplasty balloon is the removal of the balloon from the vessel. This is because when the balloon is deflated, it may tend to maintain a relatively large profile. Moreover, if the balloon includes a cutting edge, the potential exists for the cutting edge to be disposed at a large profile region of the balloon. This could subject healthy tissue to unnecessary contact with the cutting edge and resultant abrasion or cutting during the balloon removal procedure. Accordingly, there is an ongoing need for improved angioplasty devices, including cutting angioplasty balloons, with improved re-folding abilities.

SUMMARY OF THE INVENTION

The present invention relates to angioplasty balloon catheters. In at least some embodiments, an exemplary balloon catheter may include a catheter shaft having a balloon coupled thereto. The balloon may include one or more cutting members or blades. Additionally, the balloon may include a number of channels or chambers extending therethrough that may, for example, improve the folding and refolding abilities of the balloon and decrease balloon elongation. These and other features are described in more detail below.

BRIEF DESCRIPTION OF THE DRAWINGS

FIG. 4 is a cross-sectional view taken through line 4-4 in FIGS. 2 and 3;

FIG. 5 is a cross-sectional view of the device illustrated in FIG. 4, wherein the balloon is deflated;

DETAILED DESCRIPTION OF THE INVENTION

Figure 1:
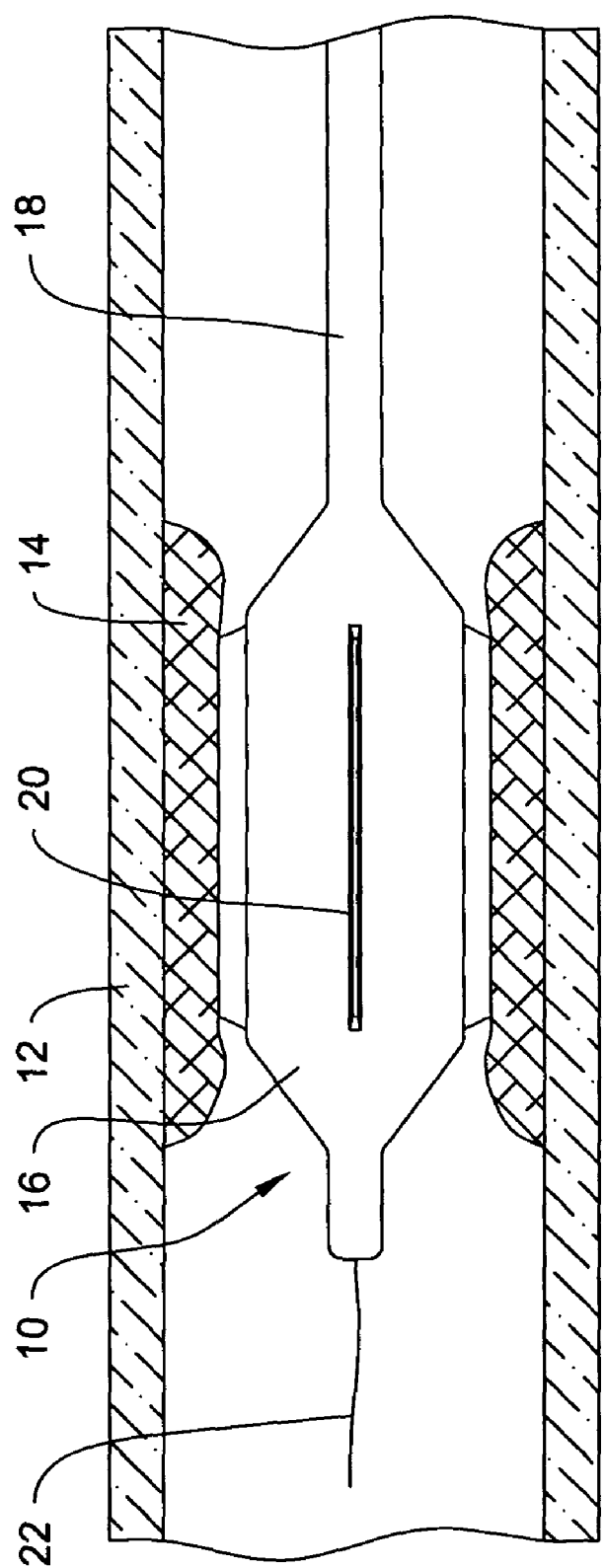
FIG. 1 is a partial cross-sectional schematic side view of an exemplary medical device disposed in a blood vessel.

The following description should be read with reference to the drawings wherein like reference numerals indicate like elements throughout the several views. The detailed description and drawings illustrate example embodiments of the claimed invention.

Angioplasty techniques that include the use of an angioplasty balloon with cutting blades attached thereto have been shown to be a desirable treatment modality for at least some intravascular interventions. FIG. 1 illustrates a distal portion of an exemplary angioplasty catheter 10 positioned in a blood vessel 12 adjacent an intravascular lesion or stenosis 14. Catheter 10 may include a balloon 16 coupled to a catheter shaft 18. Balloon 16 may include one or more cutting members 20 that can be used to cut or sever lesion 14. In general, catheter 10 may be advanced over a guidewire 22 through the vasculature to a target area. Balloon 16 can then be inflated to expand lesion 14 and cutting members 20 can cut lesion 14. The target area may be within any suitable peripheral or cardiac location.

Figure 2:
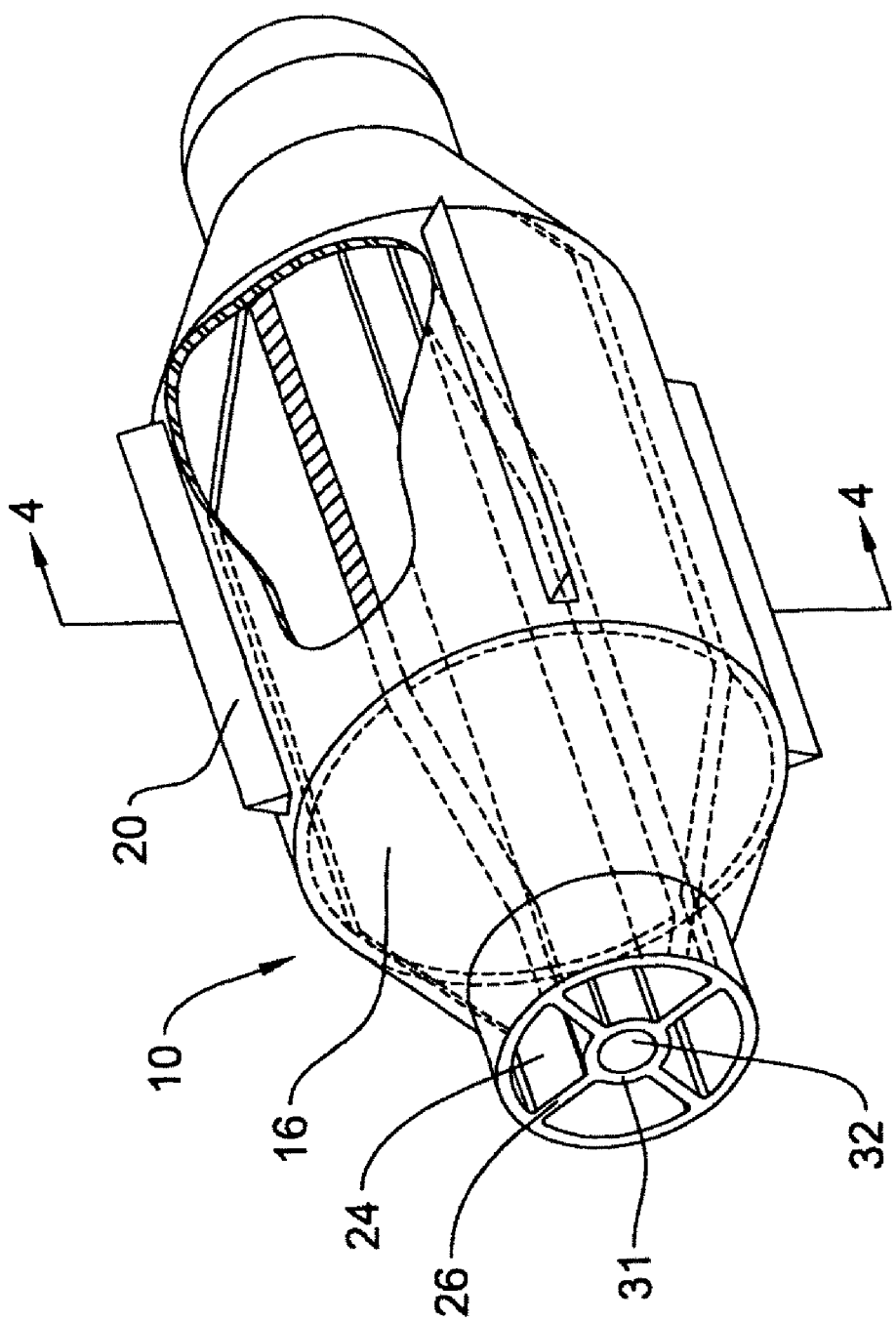
FIG. 2 is a partially cut-away perspective view of an example medical device.

A partially cut-away perspective view of a portion of catheter 10 is shown in FIG. 2. Here it can be seen that balloon 16 may include a plurality of channels or cavities 24 formed therein. The number, shape, and arrangement of cavities 24 may vary. For example, balloon 16 may include two, three, four, five, six, or more channels 24 that extend through all of or a portion of balloon 16. Channels 24 may be distributed regularly, irregularly, randomly, or in any suitable manner through balloon. Additionally, channels 24 may extend along essentially the entire length of balloon 16 or channels 24 may extend along only a portion of the balloon length.

In at least some embodiments, cavities 24 may be defined by a plurality of dividing sections 26 projecting radially inward from the interior wall of balloon 16. Sections 26 may be attached to, be integral with, or otherwise be coupled to balloon 16 and may extend between the interior wall of the balloon 16 and a central balloon tubular portion 31 which forms a lumen 32 adjacent the shaft 18. In some embodiments, shaft 18 may include an inner tubular member 28 and an outer tubular member 30 (more clearly seen in FIG. 3), and sections 26 may attach to an inner tubular member 28. In other embodiments, sections 26 may attach to an inner sleeve or tube-shaped member generally disposed over shaft 18 and/or inner tubular member 28. This tubular portion 31 which forms a lumen 32 can, in a prefered embodiment, be an integrally formed portion of the balloon 16.

Balloon 16 may be made from typical angioplasty balloon materials including polymers such as polyethylene terephthalate (PET), polyetherimid (PEI), polyethylene (PE), etc. Some other examples of suitable polymers may include polytetrafluoroethylene (PTFE), ethylene tetrafluoroethylene (ETFE), fluorinated ethylene propylene (FEP), polyoxymethylene (POM), polybutylene terephthalate (PBT), polyether block ester, polyurethane, polypropylene (PP), polyvinylchloride (PVC), polyether-ester (for example, a polyetherester elastomer such as ARNITEL® available from DSM Engineering Plastics), polyester (for example, a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example, available under the trade name PEBAX®), silicones, Marlex high-density polyethylene, Marlex low-density polyethylene, linear low density polyethylene (for example, REXELL®), polyetheretherketone (PEEK), polyimide (PI), polyphenylene sulfide (PPS), polyphenylene oxide (PPO), polysulfone, nylon, perfluoro (propyl vinyl ether) (PFA), other suitable materials, or mixtures, combinations, copolymers thereof, polymer/metal composites, and the like.

In some embodiments, it may be desirable to use high modulus or generally stiffer materials so as to reduce balloon elongation. The above list of materials includes some examples of higher modulus materials. Some other examples of stiffer materials include polymers blended with liquid crystal polymer (LCP) as well as the materials listed above. For example, the mixture can contain up to about 5% LCP. Additionally, due to the relative inelasticity of cutting members 20, balloon elongation could create shear forces between cutting members 20 and balloon 16. Thus, reducing balloon elongation may also help maintain the integrity of the coupling between balloon 16 and cutting members 20. By including channels 24 in balloon 16, it has been found possible to more precisely control the inflation, folding and refolding of balloon 16. For example, channels 24 can allow balloon 16 to be inflated more evenly, which may reduce balloon elongation. Because balloon elongation can be reduced by including channels 24, it is possible to manufacture balloon 16 from lower modulus materials, which may be easier to refold than stiffer materials.

Figure 3:
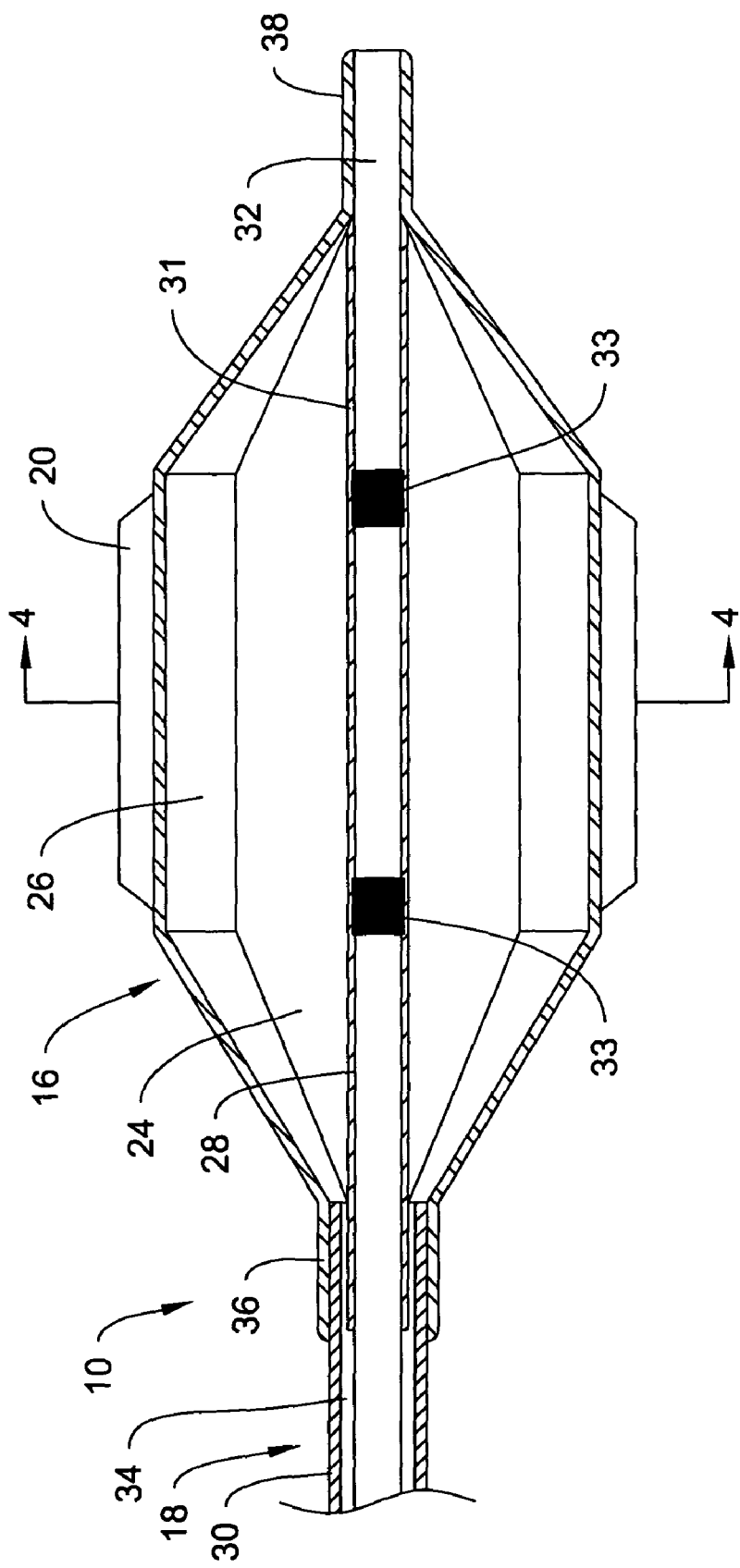
FIG. 3 is a longitudinal cross-sectional view of the device shown in FIG. 2.

Another cross-sectional view of catheter 10 is shown in FIG. 3. Here, inner tubular member 28 and outer tubular member 30 of shaft 18 can be more clearly seen. Tubular members 28/30 may be manufactured from a number of different materials. For example, tubular members 28/30 may be made of metals, metal alloys, polymers, metal-polymer composites or any other suitable materials. Some examples of suitable metals and metal alloys include stainless steel, such as 304V, 304L, and 316L stainless steel; nickel-titanium alloy such as linear-elastic or super-elastic Nitinol, nickel-chromium alloy, nickel-chromium-iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 825, or the like; or other suitable material. Some examples of suitable polymers include those described above in relation to balloon 16.

Tubular members 28/30 may be arranged in any appropriate way. For example, in some embodiments inner tubular member 28 can be disposed coaxially within outer tubular member 30. According to these embodiments, inner and outer tubular members 28/30 may or may not be secured to one another along the general longitudinal axis of catheter shaft 18. Alternatively, inner tubular member 28 may follow the inner wall or otherwise be disposed adjacent the inner wall of outer tubular member 30. Again, inner and outer tubular members 28/30 may or may not be secured to one another. For example, inner and outer tubular members 28/30 may be bonded, welded (including tack welding or any other welding technique), or otherwise secured at a bond point. In some embodiments, the bond point may be generally disposed near the distal end of catheter shaft 18. However, one or more bond points may be disposed at any position along shaft 18. The bond may desirably impact, for example, the stability and the ability of tubular members 28/30 to maintain their position relative to one another. In still other embodiments, inner and outer tubular member 28/30 may be adjacent to and substantially parallel to one another so that they are non-overlapping. In these embodiments, shaft 18 may include an outer sheath that is disposed over tubular members 28/30.

Inner tubular member 28 may include an inner lumen 32. In at least some embodiments, inner lumen 32 is a guidewire lumen. Accordingly, catheter 10 can be advanced over a guidewire to the desired location. The guidewire lumen may extend along essentially the entire length of catheter shaft 18 so that catheter 10 resembles traditional "over-the-wire" catheters. Alternatively, the guidewire lumen may extend along only a portion of shaft 18 so that catheter 10 resembles "single-operator-exchange" or "rapid-exchange" catheters.

In some embodiments, one or more marker members 33 may be coupled to catheter 10. Marker members 33 may include, be made from, be doped with, or otherwise include a radiopaque material. Radiopaque materials are understood to be materials capable of producing a relatively bright image on a fluoroscopy screen or another imaging technique during a medical procedure. This relatively bright image aids the user of catheter 10 in determining its location. Some examples of radiopaque materials can include, but are not limited to, gold, platinum, palladium, tantalum, tungsten alloy, plastic material loaded with a radiopaque filler, and the like.

Shaft 18 may also include an inflation lumen 34 that is in fluid communication with chambers 24 and may be used, for example, to transport inflation media to and from chambers 24 and/or balloon 16. The location and position of inflation lumen 34 may vary, depending on the configuration of tubular members 28/30. For example, when outer tubular member 30 is disposed over inner tubular member 28, inflation lumen 34 may be defined within the space between tubular members 28/30. Moreover, depending on the position of inner tubular member 28 within outer tubular member 30, the shape of lumen 34 (i.e., the shape adjacent shaft 18) may vary. For example, if inner tubular member 28 is attached to or disposed adjacent to the inside surface of outer tubular member 30, then inflation lumen 34 may be generally half-moon in shape; whereas if inner tubular member 28 is generally coaxial with outer tubular member 30, then inflation lumen 34 may be generally ring-shaped or annular in shape. It can be appreciated that if outer tubular member 30 is disposed alongside inner tubular member 28, then lumen 34 may be the lumen of outer tubular member 30 or it may be the space defined between the outer surface of tubular members 28/30 and the outer sheath disposed thereover.

Balloon 16 may be coupled to catheter shaft 18 in any of a number of suitable ways. For example, balloon 16 may be adhesively or thermally bonded to shaft 18. In some embodiments, a proximal portion 36 of balloon 16 may be bonded to shaft 18, for example, at outer tubular member 30, and a distal portion 38 may be bonded to shaft 18, for example, at inner tubular member 28. The exact bonding positions, however, may vary. It can be appreciated that a section of proximal portion 36 may not have sections 26 extending therefrom in order for suitable bonding between balloon 16 and outer tubular member 30. A folding spring (not shown) may be coupled to balloon 16, for example, adjacent proximal portion 36, which may further help in balloon folding and refolding. A description of a suitable folding spring can be found in U.S. Pat. No. 6,425,882, which is incorporated herein by reference. A2/////

Another cross-sectional view of balloon 16 is shown in FIG. 4. Similar to what is shown in the other figures, it can be seen that balloon 16 may include four chambers 24 and four dividing sections 26. Of course, the number and arrangement of chambers 24 and sections 26 may vary, as stated above. It can also be seen here that sections 26 may have dividing walls that project inwardly and connect to a tubular inner sleeve portion 44 of balloon 16 that may be, for example, configured to attach to shaft 18 and/or inner tubular member 28. Alternatively, balloon 16 may not include inner sleeve portion 44 and, instead, projections may attach directly to tubular member 28. inner Sleeve portion 44 may be made from the same materials as balloon 16 and can be integrally formed or it may be made from different materials.

FIG. 5 illustrates balloon 16 in a deflated configuration. Venting inflation media from balloon 16 allows balloon 16 to re-fold inwardly into a collapsed, deflated configuration. In addition or as an alternative to this feature, a vacuum can be applied to chambers 24 (e.g., by applying a vacuum to lumen 34) in order to facilitate their collapse. This may allow balloon 16 to re-fold to a consistent and predictable configuration where, for example, cutting members 20 are moved radially inward and one or more "wings" or flaps are defined in balloon 16. By forming wings, balloon 16 may have a lower profile so that balloon 16 may be easily removed from the vasculature. Additionally, it may be possible for the wings to fold over cutting members 20 so as to guard healthy vascular tissue from unplanned contact with cutting members 20.

Figure 6:
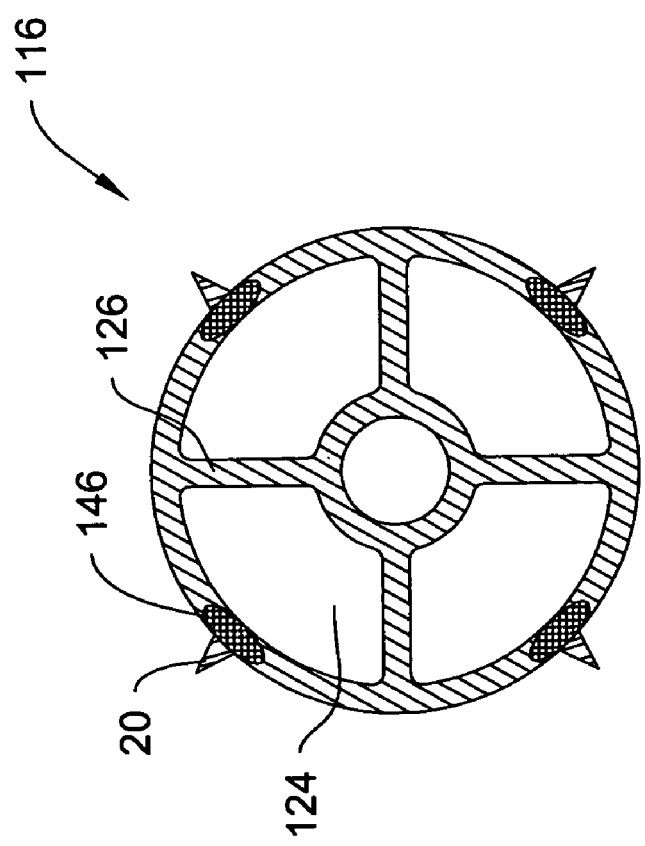
FIG. 6 is a cross-sectional view of another example medical device.

A cross-sectional view of another example balloon 116, suitable for use with catheter 10 and other medical devices, is shown in FIG. 6. Balloon 116 is similar to balloon 16, except that balloon 116 may include a plurality of stiffened regions 146. Stiffened regions 146 may generally be sections of balloon 116 that are configured to provide additional structural support, for example, adjacent cutting members 20. This additional structural support may be desirable by facilitating the coupling of cutting members 20 to balloon 16 and by providing support so that cutting members 20 remain secured to balloon 16 during placement and use of balloon 16. In some embodiments, stiffened regions 146 may be defined by blending or adding LCP or any other suitably stiff material (including polymers and metals) with balloon 16. Any suitable means of stiffening may be included without departing from the spirit of the invention.

Figure 7:
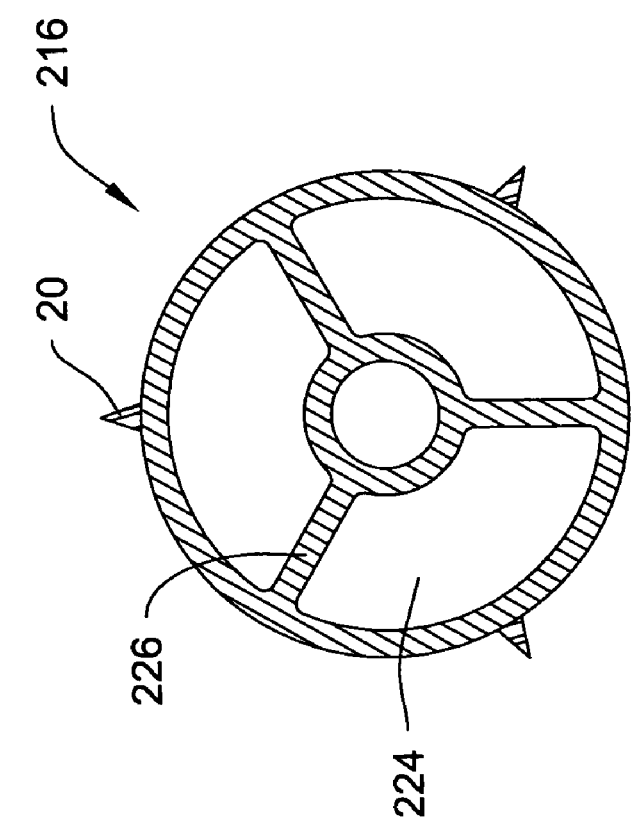
FIG. 7 is a cross-sectional view of another example medical device.
Figure 8:
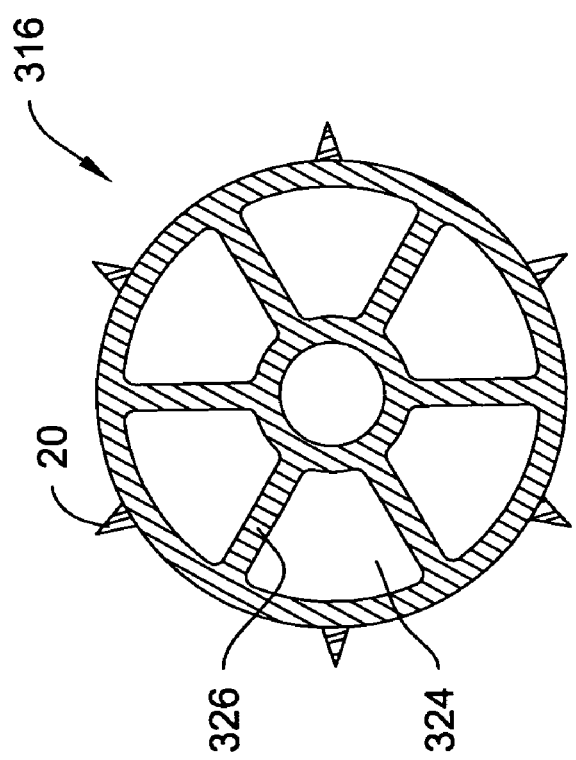
FIG. 8 is a cross-sectional view of another example medical device.

FIGS. 7 and 8 illustrate additional example balloons 216/316 that have varying numbers of chambers 224/324 and sections 226/326. For example, FIG. 7 illustrates balloon 216 having three chambers 224 and three sections 226. FIG. 8 illustrates balloon 216 having six chambers 324 and six sections 326. These example illustrations are meant to show that essentially any number of chambers 224/324 and sections 226/326 may be included in any of the various embodiments of balloons described herein.

Figure 9:
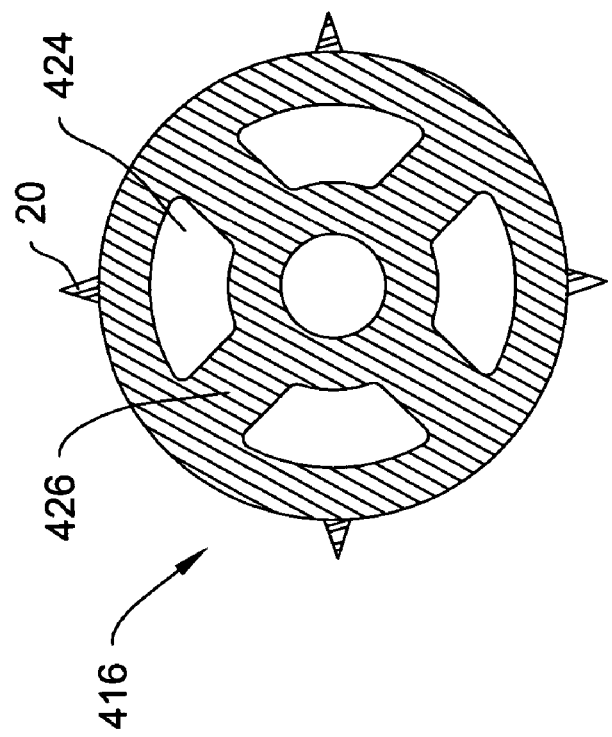
FIG. 9 is a cross-sectional view of another example medical device.

Another example balloon 416 is shown in FIG. 9. Balloon 416 is similar to other balloons described herein, except that chambers 424 and dividing sections 426 are defined within the wall of balloon 416. According to this embodiment, balloon 416 may be somewhat thicker than typical angioplasty balloons so that chambers 424 can be formed therein. The additional thickness may be desirable for a number of reasons. For example, thickened balloon 416 may have improved longitudinal stability and, thus, be less likely to elongate.

Figure 11:
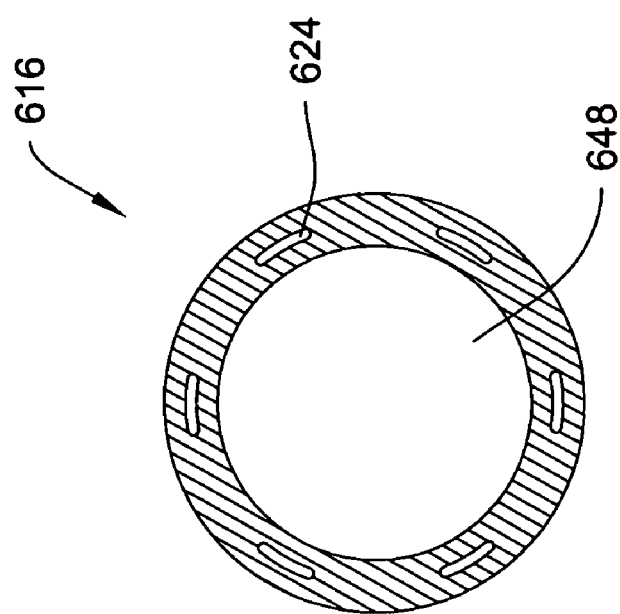
FIG. 11 is a cross-sectional view of an alternative balloon tube used to form a multi-chamber balloon medical device.
Figure 10:
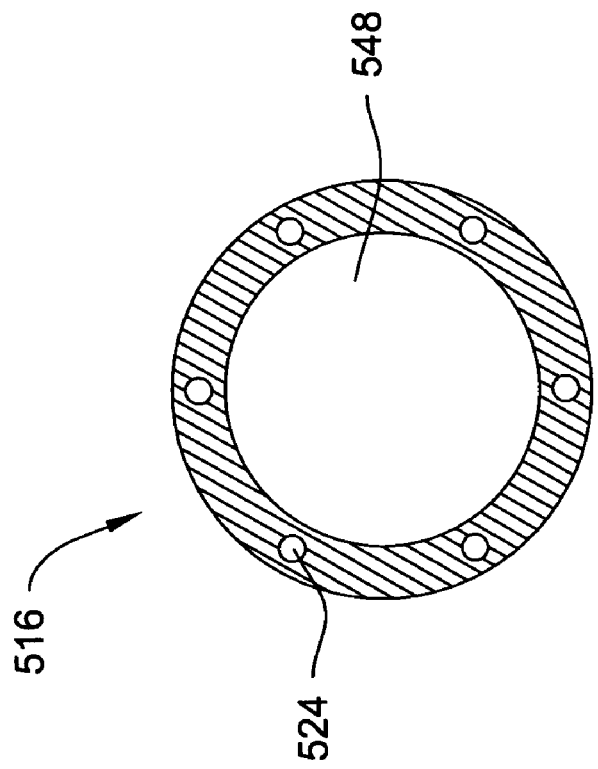
FIG. 10 is a cross-sectional view of an extruded balloon tube used to form a multi-chamber balloon.

FIG. 10 is a cross-sectional view of an extruded tubular member that can be used to form a balloon of the present invention. Balloon tube 516 is similar to other balloons described herein and may include lumens 524 formed in the balloon wall. As it can be seen, lumens 524 may be round in shape and can be dispersed regularly throughout the balloon wall. However, chambers 524 can have essentially any appropriate shape, can vary in number, and can be dispersed in any pattern in the balloon wall. FIG. 11 shows one such alternative embodiment of a balloon tube 616 with wall lumens 624 formed during extrusion that are oval or pill-shaped.

The balloon tubes 516 or 616 are used to form balloons of preferred embodiments of the present invention. The balloon tube is placed within a mold chamber that has a preferred exterior shape for the balloon. The balloon tube is heated and expanded utilizing a gas or liquid such that the expanded chambers are formed from the lumens 524 or 624. The wall thicknesses of the balloon material surrounding the lumens are selected such that thinning occurs during expansion in the mold, but not to a degree that compromises burst pressure of the final balloon product. The various balloon tube lumens may be inflated individually or simultaneously to form final chambers of desired dimension in the overall balloon cross section.

As stated above, including a plurality of chambers in the balloon with dividing sections extending radially between chambers may help to reduce balloon elongation. Additionally, the chambers and walls between the chambers may also be desirable by facilitating re-folding. For example, the chambers can be vented by pulling vacuum or other means so as to partially collapse the balloon which will preferentially fold first at the thinner areas between dividing sections. At these creases, the balloon can more easily and consistently re-fold when the entire balloon is deflated. By placing the cutting blades to extend longitudinally at a circumferential position between the wall dividing sections or chambers, the cutting blades will be preferentially drawn radially inward away from the vessel wall during deflation. In some preferred embodiments, the blades are positioned at about the circumferential mid-point between adjacent walls forming a chamber as depicted in FIGS. 4 and 5.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:
1. A medical device, comprising:
an elongate shaft;
an expandable balloon coupled to the shaft, the balloon including an inside surface;
wherein the shaft includes an outer tubular member, an inner tubular member, and a single common inflation lumen disposed therebetween;

a plurality of dividing sections extending radially inward from the inside surface of the balloon to define a plurality of chambers in the balloon, each of the chambers extending along essentially the entire length of the balloon;

one or more cutting members coupled to the balloon; and wherein the single common inflation lumen is in fluid communication with all of the chambers of the balloon.

2. The device of claim 1, wherein the inner tubular member includes an inner lumen extending at least partially therethrough.

3. An angioplasty balloon catheter, comprising:

a catheter shaft, the shaft including an inner tubular member having an inner lumen extending therethrough, an outer tubular member, and a single common inflation lumen disposed between the inner and outer tubular members;

an expandable balloon coupled to the shaft, the balloon including a balloon wall and a plurality of inner chambers each extending along essentially the entire length of the balloon;

wherein the inflation lumen is in fluid communication with all of the inner chambers; and at least one cutting member coupled to the outer wall of the balloon.

4. The catheter of claim 3, wherein the balloon includes three inner chambers.

5. The catheter of claim 3, wherein the balloon includes four inner chambers.

6. An angioplasty balloon catheter, comprising:

a catheter shaft;

a multi-chamber balloon coupled to the shaft, each of the chambers extending along essentially the entire length of the balloon, the balloon including an inner sleeve, an outer wall, and a plurality of internal wall segments extending between the inner sleeve and the outer wall;

wherein the shaft includes a single common inflation lumen that supplies inflation media to each chamber of the multi-chamber balloon; and one or more longitudinally extending cutting members coupled to the outer wall of the balloon at circumferential locations between adjacent internal wall segments.

7. The catheter of claim 6, wherein the balloon includes three internal wall segments and three chambers defined between adjacent pairs of internal wall segments.

8. The catheter of claim 6, wherein the balloon includes four internal wall segments and four chambers defined between adjacent pairs of internal wall segments.

9. A method of using a cutting balloon catheter, comprising the steps of:

providing a cutting balloon catheter, the catheter including a catheter shaft and a multi-chamber cutting balloon coupled to the shaft, the multi-chamber balloon including an inner sleeve, an outer wall, a plurality of internal wall segments extending between the inner sleeve and the outer wall, a plurality of chambers defined between pairs of internal wall segments, each chamber extending along essentially the entire length of the balloon, and one or more cutting members coupled to the outer surface of the balloon between adjacent internal wall segments;

advancing the cutting balloon catheter through a blood vessel to a position adjacent an area of interest;

inflating the balloon by infusing inflation media into the chambers, wherein inflating the balloon includes inflating each chamber of the multi-chamber cutting balloon through a single common inflation lumen;

deflating the balloon by venting the inflation media from the chambers to preferentially draw the cutting members radially inward; and withdrawing the cutting balloon catheter from the blood vessel.

10. The method of claim 9, wherein the step of deflating the balloon by venting the inflation media from the chambers includes applying a vacuum to the chambers.

* * * * *

UNITED STATES PATENT AND TRADEMARK OFFICE
CERTIFICATE OF CORRECTION

| | | |
|---|---|---|
| PATENT NO. | : 7,887,557 B2 | |
| APPLICATION NO. | : 10/641955 | |
| DATED | : February 15, 2011 | |
| INVENTOR(S) | : Gregory S. Kelley et al. | |

It is certified that error appears in the above-identified patent and that said Letters Patent is hereby corrected as shown below:

Column 3
Line 8, delete "prefered", and insert therefor -- preferred --.

Signed and Sealed this
Twenty-first Day of June, 2011

David J. Kappos
*Director of the United States Patent and Trademark Office*